United States Patent [19]
Hardt et al.

[11] Patent Number: 5,488,163
[45] Date of Patent: Jan. 30, 1996

[54] PROCESS FOR THE PRODUCTION OF 4, 4'-(PHENYLENE-DIISOPROPYL)-BIS(2, 6-DIALKYLANILINES)

[75] Inventors: Peter Hardt, Visp; Ulrich Daum, Hofstetten; Theodor Völker, Marly, all of Switzerland

[73] Assignee: Lonza Ltd., Gampel/Valais, Switzerland

[21] Appl. No.: 360,082

[22] Filed: Dec. 20, 1994

Related U.S. Application Data

[62] Division of Ser. No. 137,972, Oct. 19, 1993, abandoned.

[30] Foreign Application Priority Data

Oct. 21, 1992 [CH] Switzerland .............................. 3264/92

[51] Int. Cl.$^6$ ................................................ C07C 209/68
[52] U.S. Cl. ........................................................ 564/315
[58] Field of Search .............................................. 564/315

[56] References Cited

U.S. PATENT DOCUMENTS

| | | | |
|---|---|---|---|
| 3,200,152 | 8/1965 | Ruppert et al. | 260/570 |
| 3,311,660 | 3/1967 | Krimm et al. | 260/570 |
| 3,365,347 | 1/1968 | Lund et al. | 260/570 |
| 3,424,795 | 1/1969 | Lund et al. | 260/570 |
| 4,374,272 | 2/1983 | Yuasa et al. | 564/315 |
| 4,973,754 | 11/1990 | Li | 564/315 |

FOREIGN PATENT DOCUMENTS

| | | |
|---|---|---|
| 0322974 | 7/1989 | European Pat. Off. . |
| 0492473 | 7/1992 | European Pat. Off. . |
| 6408539 | 1/1965 | Netherlands . |

Primary Examiner—Peter O'Sullivan
Attorney, Agent, or Firm—Fisher, Christen & Sabol

[57] ABSTRACT

A process for the production of 4,4'-(phenylenediisopropyl)bis(2,6-dialkylanilines) of the general formula:

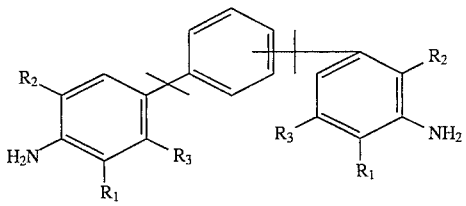

wherein $R_1$ and $R_2$ are the same or different and each is a $(C_1-C_4)$alkyl group, $R_3$ is hydrogen or halogen, and the central phenylene function is substituted in the 1,3 or 1,4 position, by reaction of a corresponding diisopropyl benzene with a corresponding aniline in the presence of catalytic amounts of aluminum chloride. The 4,4'-(phenylenediisopropyl)-bis(2,6-dialkylanilines) are used as cross-linking agents for epoxy resins, as chain lengthening agents for polyurethanes, for the production of hydrolysis protective agents for polyurethanes, or for the production of UV stabilizers in varnishes.

4 Claims, No Drawings

PROCESS FOR THE PRODUCTION OF 4, 4' -(PHENYLENE-DIISOPROPYL)-BIS(2, 6-DIALKYLANILINES)

This is a divisional application of Ser. No. 08/137,972, filed Oct. 19, 1993 now abandoned.

BACKGROUND OF THE INVENTION

1. Field of the Invention

The invention relates to a new process for the production of 4,4'-(phenylenediisopropyl)-bis(2,6-dialkylanilines) of the general formula:

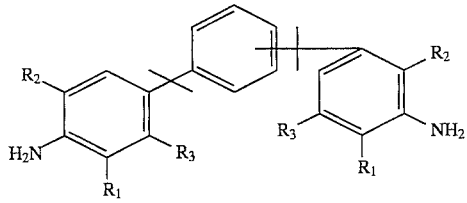

wherein $R_1$ and $R_2$ are the same or different and each is a $(C_1–C_4)$-alkyl group, $R_3$ is a hydrogen or halogen atom, and the central phenylene function is substituted in the 1,3 or 1,4 position, to 4,4'-(phenylene-1,3-diisopropyl)-bis(2,6-dialkylaniline) derivatives not yet described in the prior art and to the use of the mentioned bis-anilines as cross-linking agents for epoxy resins, as chain lengthening agent for polyurethanes, for the production of hydrolysis protective agents for polyurethanes and for the production of UV stabilizers in varnishes.

2. Background Art

A production method for 4,4'-(phenylenediisopropyl)-bisanilines is disclosed in Dutch Published Patent Application No. 6408539. The reaction of aniline, which is in great excess, with 1,4-diisopropenyl benzene in the presence of toluene or benzene as a solvent and activated alumina as a catalyst is described therein. In addition to the necessary large aniline excess, the very long reaction time of approximately 16 hours is a great drawback for an industrial process. Furthermore, the activated alumina catalysts are not well-defined compounds so that the reproducibility of the reactions is problematical.

Another variant for the production of 4,4'-(phenylenediisopropyl)-bis-anilines is disclosed in U.S. Pat. No. 3,200,152. As can be seen, especially from Example 5, the reaction of aniline with 1,3-diisopropylene benzene takes place in the presence of aniline-HCl in a reaction time of less than one hour at a very good yield of 92 percent. However, the tests of the present inventors have shown that this variant is unusable for the reaction of 2,6-dialkylanilines.

BROAD DESCRIPTION OF THE INVENTION

In view of the fact that the processes of the prior art have the above-mentioned drawbacks, the main objective of the invention was to provide a simple, economical and industrially feasible process which overcomes or avoids such drawbacks. The main object could be achieved in a surprisingly simple way with the process according to the invention.

Other objectives and advantages of the invention are set out herein or are obvious herefrom to one skilled in the art.

The objectives and advantages of the invention are achieved by the processes and compounds of the invention.

The invention involves a process for the production of 4,4'-(phenylenediisopropyl)-bis(2,6-dialkylanilines) of the general formula:

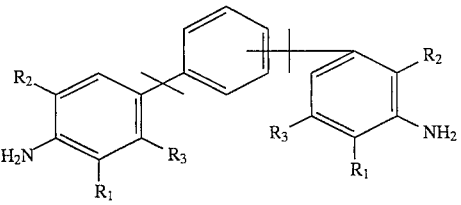

wherein $R_1$ and $R_2$ are the same or different and each is a $(C_1–C_4)$-alkyl group, $R_3$ is a hydrogen or halogen atom, and the central phenylene function is substituted in the 1,3 or 1,4 position. The process includes reacting a diisopropenyl benzene of the general formula:

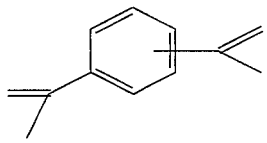

wherein the isopropenyl groups on the aromatic nucleus are in the 1,4 or 1,3 position to one another, in the presence of aluminum chloride as the catalyst with an aniline of the general formula:

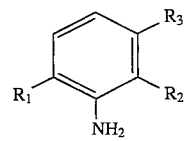

wherein $R_1$, $R_2$ and $R_3$ have the above-mentioned meanings.

Preferably the reaction is carried out with exclusion of water at a temperature between 120° and 200° C. Preferably the aluminum chloride is used in an amount of 0.02 to 0.3 mol, relative to 1 mol of the aniline of the general formula III. Preferably the diisopropenyl benzene of the general formula II, relative to the aniline of general formula III, is used in an excess of 10 to 100 percent.

The invention also involves 4,4'-(phenylene-1,3-diisopropyl) -bis(2,6-dialkylanilines) of the general formula:

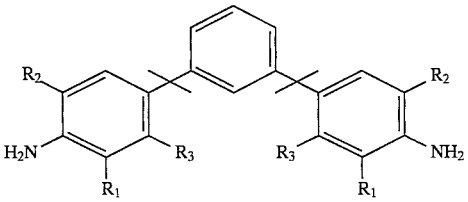

wherein $R_1$, $R_2$ and $R_3$ have the above-mentioned meanings in the general formula I.

Preferably, in the 4,4'-(phenylene-1,3-diisopropyl)-bis(2, 6-dialkylanilines) of the general formula IV, $R_1$ and $R_2$ are the same or different and each is a methyl group, ethyl group or isopropyl group, and $R_3$ is a hydrogen atom or a chlorine atom.

The invention also involves using the 4,4'-(phenylenediisopropyl) -bis(2,6-dialkylaninlines) of the general formula I as cross-linking agents in epoxy resins. The invention involves using the 4,4'-(phenylenediisopropyl)-bis(2,6-dialkylanilines) according to the general formula I as chain lengthening agents in polyurethanes.

The invention further involves using the 4,4'-(phenylenediisopropyl) -bis(2,6-dialkylanilines ) according to the general formula I for the production of hydrolysis protective agents for polyurethanes. The invention involves using the 4,4'-(phenylenediisopropyl) -bis(2,6-dialkylanilines) according to the general formula I for the production of UV stabilizers in varnishes.

DETAILED DESCRIPTION OF THE INVENTION

Details of the meaning of the radicals $R_1$, $R_2$ and $R_3$ in general formulas I, III and IV is as follows:

As the ($C_1$–$C_4$) alkyl group for $R_1$ and $R_2$, suitably a methyl, ethyl, n-propyl, i-propyl, n-butyl, i-butyl or t-butyl group is used. In the case where $R_1$ and $R_2$ have a different meaning, the mentioned alkyl groups can be varied at will. Preferred combinations where $R_1$ is not the same as $R_2$ are methyl and ethyl or methyl and i-propyl.

With $R_1$ and $R_2$ having the same meaning, basically all of the mentioned alkyl groups can be used; $R_1$ and $R_3$ are preferably methyl, ethyl or i-propyl.

The halogen of $R_3$ can be fluorine, chlorine, bromine or iodine. The preferred halogen of $R_3$ is chlorine.

When $R_3$ is halogen, it can enter all the mentioned combinations with $R_1$ and $R_2$. Preferred combinations of $R_3$ having the preferred meaning of chlorine with $R_1$ and $R_2$ are:

| | | |
|---|---|---|
| $R_1$ = methyl | $R_2$ = ethyl | $R_3$ = chlorine |
| $R_1$ = ethyl | $R_2$ = methyl | $R_3$ = chlorine |
| $R_1$ = methyl | $R_2$ = isopropyl | $R_3$ = chlorine |
| $R_1$ = i-propyl | $R_2$ = methyl | $R_3$ = chlorine |
| $R_1$ = methyl | $R_2$ = methyl | $R_3$ = chlorine |
| $R_1$ = ethyl | $R_2$ = ethyl | $R_3$ = chlorine |
| $R_1$ = isopropyl | $R_2$ = isopropyl | $R_3$ = chlorine |

The starting material of the process is a diisopropenyl benzene of the general formula:

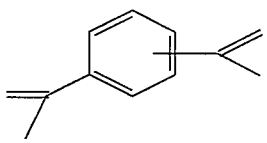

II which is suitably used in an excess of 10 to 100 percent, relative to the aniline of the general formula:

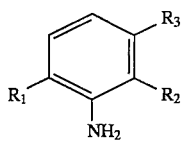

III wherein $R_1$, $R_2$ and $R_3$ have the above-mentioned meanings.

Aluminum chloride is used in catalytic amounts of usually 0.02 to 0.3 mol, preferably 0.05 to 0.20 mol, relative to 1 mol of the aniline of general formula III used.

The reaction advantageously takes place with the exclusion of water and without additional solvent at a reaction temperature of 120° to 200° C., preferably 140° to 160° C. Optionally an additional inert solvent can be added, but, as a rule, this does not provide any advantages. The reaction takes place very quickly and, as a rule, is completed after a maximum of 2 hours. The desired 4,4'-(phenylenediisopropyl)-bis(2,6-dialkylaniline) can then be isolated from the reaction mixture according to ways known to one skilled in the art.

The 4,4'-(phenylene-1,3-diisopropyl)-bis(2,6-dialkylanilines) of the general formula:

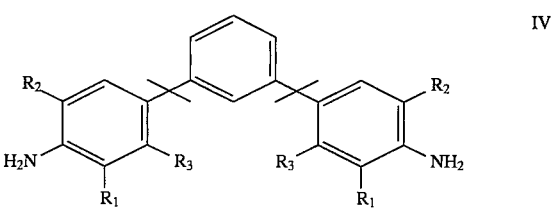

IV wherein $R_1$, $R_2$ and $R_3$ have the above-mentioned meanings, are made available according to the process of the invention. Such compounds have not previously been described in the prior art.

Especially preferred representatives of the 4,4'-(phenylene-1,3-diisopropyl) -bis(2,6-dialkylanilines) of general formula IV are:

4,4'-(phenylene-1,3-diisopropyl)-bis(2,6-diisopropylaniline), 4,4'-(phenylene-1,3-diisopropyl)-bis(2-isopropyl-6-methylaniline), 4,4'-(phenylene-1,3-diisopropyl)-bis(2-ethyl-6-methylaniline), 4,4'-(phenylene-1,3-diisopropyl)-bis(2,6-diethylaniline ), and 4,4'-(phenylene-1,3-diisopropyl)-bis(3-chloro-2,6-diethylaniline).

The individual compounds are distinguished by the versatility in their use for special polymers, such as, for epoxides and polyurethanes. Both the phenylene-1,3-diisopropyl and the phenylene-4-diisopropyl derivatives are well suited as cross-linking agents for epoxy resins, as chain-lengthening agents in polyurethanes, after usual reaction to the corresponding carbodiimides as hydrolysis protective agents for polyurethanes, and after usual reaction to the corresponding oxalic acid amide derivatives as UV stabilizers in varnishes.

EXAMPLE 1

Production of 4,4'-(phenylene-1,3-diisopropyl)bis(2,6-diisopropylaniline)

88.69 g of 2,6-diisopropylanaline (0.5 mol) and 6.69 g of aluminum chloride (0.05 mol) were added in succession in a 500 ml reaction vessel with blade agitator, thermometer, reflux condenser and dropping funnel with exclusion of moisture. The mixture was heated to 155° C. and mixed with 79.15 g of 1,3-diisopropenyl benzene (0.5 mol) through a dropping funnel for 2 hours. It was allowed to cool, mixed with 200 ml of hexane and 80 ml of sodium hydroxide solution (20%) and allowed to stir until two clear phases had developed after approximately 60 minutes. After separation of the phases, the upper hexane phase was saturated with HCl gas in a 1 1-reaction vessel after addition of 300 ml of hexane, the precipitated precipitate was collected on a nutsch, pressed well, and suspended in 300 ml of toluene. 200 ml of sodium hydroxide solution (20%) was carefully added and 2 clear phases were obtained. The separated toluene phase was freed from solvent by vacuum distillation. From the yellowish brown, partially crystalline evaporation residue, 105.31 g of 4,4'-(phenylene-1,3-diisopropyl )-his(2, 6-diisopropylaniline), which was first liquid and then quickly solidified, was obtained by flash distillation (210° C./0.2 mbar). The yield of product was 82.1 percent. The product had a melting point of 107° to 108° C. (ethanol). Other data concerning the product was:

$^1$HNMR: ($CDCl_3$, 300 MHz) in ppm
1.20, d, 24H, J=6.9 Hz;

1.61, s, 12H;
2.90, sept, 4H, J=6.9 Hz;
3.59, s, 4H;
6.88, s, 4H;
6.99, m, 2H;
7.10, m, 1H;
7.19, m, 1H.

EXAMPLE 2

Production of 4,4'-(phenylene-1,3-diisopropyl)bis (2-isopropyl-6-metyhlaniline)

As in Example 1, 25.50 g of 2-isopropyl-4-methylaniline (0.17 mol) and 2.09 g of aluminum chloride (0.016 mol) were heated to 155° C. and mixed with 15.81 g of diisopropenyl benzene for 40 minutes After cooling to 80° C. addition of 250 ml of hexane and 50 ml of sodium hydroxide solution (10%), it was stirred, at 55° to 60°, until two clear phases had developed. A white crystallizate was precipitated from the separated hexane phase with cooling and allowed to stand at 0° C. After filtering off by suction and drying, 29.55 g of white crystalline 4,4'-(phenylene-1,3-diisopropyl)-bis(2-isopropyl-4-methylaniline) was obtained. The yield of product was 76.1 percent. The product had a melting point of 89° to 90° C. Other data concerning the product was:

$^1$HNMR: (CDCl$_3$, 300 MHz) in ppm
1.19, d, 12H, J=6.9 Hz;
1.60, s, 12H;
2.13, s, 6H;
2.88, sept, 2H, J=6.9 Hz;
3.47, s, 4H;
6.77, d, 2H, J=2.3 Hz;
6.87, d, 2H, J=2.3 Hz;
7.00, m, 2H;
7.11, m, 1H;
7.22, m, 1H.

EXAMPLE 3

Production of 4,4'-(phenylene-1,3-diisopropyl)bis(2-ethyl-4-methylaniline) 6.76 g of 2-ethyl-6-methylaniline (0.05 mol) and 0.67 g of aluminum chloride (0.005 mol) were mixed with 4.76 g of 1,3-diisopropenyl benzene (0.030 mol) at 160° C. for 30 minutes and worked up corresponding to Example 2. 7.81 g of 4,4'-(phenylene-1,3-diisopropyl)-bis(2-ethyl-4-methylaniline) was obtained. The yield of product was 72.9 percent. The product had a melting point of 114° to 115° C. Other data concerning the product was:

$^1$HNMR: (CDCl$_3$, 300 MHz ) in ppm
1.17, t, 6H, J=7.5 Hz;
1.60, s, 12H;
2.12, s, 6H;
2.47, q, 4H, J=7.5 Hz;
3.47, s, 4H;
6.77, s, 4H;
7.01, m, 2H;
7.12, m, 1H;
7.24, m, 1H.

EXAMPLE 4

Production of 4,4'-(phenylene-1,3-diisopropyl)bis(2.6-diethylaniline)

14.95 g of 2,6-diethylaniline (0.10 mol) was mixed with 1.40 g of aluminum chloride, heated to 150° C. and mixed with 9.68 g of 1,3-diisopropenyl benzene (0.061 mol) for 20 minutes. After cooling to 60° C. it was stirred at this temperature after mixing with 500 ml of hexane and 20 ml of sodium hydroxide solution (20%) until two clear phases had developed. The crystalline precipitate precipitated during the cooling was separated and dried. 17.66 g of white, crystalline 4,4'-(phenylene-1,3-diisopropyl)-bis(2,6-diethylaniline) was obtained. The yield of product was 77.3 percent. The product had a melting point of 118° to 119° C. Other data concerning the product was:

$^1$HNMR: (CDCl$_3$, 300 MHz) in ppm
1.18, t, 12H, J=7.5 Hz;
1.61, s, 12H;
2.48, q, 8H, J=7.5 Hz;
3.51, s, 4H;
6.79, s, 4H;
7.01, m, 2H;
7.12, m, 1H;
7.24, m, 1H.

EXAMPLE 5 (Comparison Example)

According to U.S. Pat. No. 3,200,152, Example 5, 160.3 g of 2,6-diisopropylaniline hydrochloride (0.75 mol), 44.3 g of 2,6-diisopropylaniline (0.25 mol) and 39.6 g of 1,3-diisopropenyl benzene (0.25 mol) were heated for 40 minutes to 180° to 230° C. In the organic phase obtained after addition of sodium hydroxide solution, only 2,6-diisopropylaniline and 1,3-diisopropenyl benzene, but no 4,4'-(phenylene-1,3.-diisopropyl)-bis(2,6-diisopropylaniline), were able to be detected.

EXAMPLE 6

Production of 4,4'-(phenylene, 1,4-diisopropyl)bis(2,6-diethylaniline )

15.02 g of 2,6-diethylaniline (0.10 mol), 1.58 g of aluminum chloride (0.012 mol) and 10 ml of heptane were heated to 80° C. and mixed at this temperature for 10 minutes with a solution of 10.80 g of 1,4-diisopropenyl benzene (0.07 mol) in 40 ml of heptane. The obtained clear solution was converted in an autoclave and heated for 1.5 hours to 150° C. It was allowed to cool to about 60° C. and the content of the autoclave was added to a mixture of 200 ml of heptane and 50 ml of sodium hydroxide solution (30%) and allowed to stir with light heating until two clear phases had developed. The still warm upper heptane phase was separated, washed again with water and left standing at 0° C. for 1 to 2 days. The precipitated crystallizate was collected on a nutsch, washed again briefly with heptane and dried at 65° C. and 20 mbar. 15 g of crystalline almost white 4,4'-(phenylene-1,4 -diisopropyl)bis(2,6-diethylaniline) was obtained. The yield of the product was 65.7 percent. By recycling of the crystallation mother liquor, the yield could be increased to 80 to 85 percent. The product had a melting point of 115.5° to 116° C. Other data for the product was:

$^1$HNMR: (CDCl$_3$, 400 MHz) in ppm
1.19t, 12H, J=7.6 Hz;
1.63 s, 12H;
2.48 g, 8H, J=7.6 Hz;
3.51 s, 4H;
6.81 s, 4H;
7.12 s, 4H.

EXAMPLE 7

Production of 4,4'-(phenylene-1,4-diisopropyl)bis(2-ethyl-6-methylaniline)

As in Example 6, 13.59 g of 2-ethyl-6-methylaniline (0.10 mol) was reacted in the presence of 1.53 g of aluminum chloride (0.012) with 10.74 g of 1,4-diisopropenyl benzene (0.07 mol). The product was worked up correspondingly. 16.32 g of crystalline almost white 4,4'-(phenylene-1,4-diisopropyl)-bis(2-ethyl-6-methylaniline) was obtained. The yield of the product was 76.1 percent. The product had a melting point of 114° to 116.5° C. Other data concerning the product was:

$^1$HNMR: (CDCl$_3$, 400 MHz) in ppm
1.18 t, 6H, J=7.5 Hz;
2.13 s, 12H;
2.48 q, 4H, J=7.5 Hz;
3.47 s, 4H;
6.81 s, 4H;
7.12 s, 4H.

EXAMPLE 8

Production of 4,4'-(phenylene-1,4-diisopropyl)bis(2-isopropyl-6-methylaniline)

23.9 g of 2-isopropyl-6-methylaniline (0.16 mol) and 2.13 g (0.016 mol) of aluminum chloride was heated to 150° C. and mixed with 15.8 g of 1,4-diisopropenyl .benzene (0.10 mol) for 35 minutes It is allowed to cool to 50° C. mixed with 250 ml of hexane and 50 ml of sodium hydroxide solution (20%) and allowed to stir until two clear phases had developed. The upper phase was washed with water. When left standing at −5° to 0° C., a white crystallizate was precipitated. After the separation and drying, 26.64 g of 4,4'-(phenylene-1,4-diisopropyl)-bis(2-isopropyl-6-methylaniline) was obtained. The yield of the product was 72.9 percent. The product had a melting point of 112° to 121° C. Other data concerning the product was:

1HNMR: (CDCl$_3$, 400 MHz) in ppm
1.20 d, 12H, J=6.8 Hz;
1.63 s, 12H;
2.13 s, 6H
2.88 s, 2H, J=6.8 Hz;
3.51 s, 4H;
6.78 d, 2H, J=2.2 HZ;
6.90 d, 2H, J=2.2 HZ;
7.12 s, 4H.

EXAMPLE 9

Production of 4,4'-(phenylene-1,4-diisopropyl)bis(2,6-diisopropylaniline).

As in Example 6, 17.69 g of 2,6-diisopropylaniline (0.10 tool) in the presence of 1.63 g of aluminum chloride (0.012 mol) was reacted with 10.75 g of 1,4-diisopropenyl benzene (0.068 mol). The product was worked up correspondingly. 13.74 g of almost white 4,4'-(phenylene-1,4-diisopropyl)-bis(2,6-diisopropylaniline) was obtained. The yield of the product was 53.6 percent. By recycling of the mother liquor, it was possible to increase the yield to 75 to 80 percent. The product had a melting point of 123° to 129° C. Other data concerning the product was:

$^1$HNMR: (CDCl$_3$, 400 MHz) in ppm
1.20 d, 24H, J=6.8 Hz
1.62 s, 12H;
2.90 s, 4H, J=6.8 Hz;
3.59 s, 4H;
6.89 s, 4H
7.11, s, 4H.

EXAMPLE 10

Production of 4,4'-(phenylene-1,4-diisopropyl)bis(2,6-dimethylaniline)

As in Example 6, 12.18 g of 2,6-dimethylaniline (0.10 mol) in the presence of 1.61 g of aluminum chloride (0.012 mol) was reacted with 10.72 g of 1,4-diisopropenyl benzene (0.68 mol). The product was worked up correspondingly. 12.48 g of crystalline 4,4'-(phenylene-1,4-diisopropyl)-bis(2,6-dimethyllaniline) was obtained. The yield of the product was 62.3 percent. By working up of the mother liquor, an additional 5.1 g of the product was obtained so that the total yield increased to 88 percent. The product had a melting point of 149.5° to 150.5° C. Other data concerning the product was:

$^1$HNMR: (CDCl$_3$, 400 MHz) in ppm
1.61 s, 12H
2.12 s, 12H
3.44 s, 4H
6.80 d, 4H
7.11 s, 4H.

Testing of the 4,4'-(phenylenediisopropyl)bis(2,6-dialkylanilines)

I. Tested compounds:
1. 4,4'-(phenylene-1,3-diisopropyl)-bis(2-ethyl-6-methylaniline), termed 1,3 DIPMEA
2. 4,4'-(phenylene-1,3-diisopropyl )-bis(2,6-diethylaniline), termed 1,3 DIPDEA
3. 4,4'-(phenylene-1,3-diisopropyl)-bis(2-isopropyl-6-methylaniline), termed 1,3 DIPMIPA
4. 4,4'-(phenylene-1,3-diisopropyl)-bis(2,6-diisopropylaniline), termed 1,3 DIPDIPA
5. 4,4'-(phenylene-1,4-diisopropyl)-bis(2,6-diethylaniline), termed 1,4 DIPDEA II. Testing of the compounds mentioned in I as cross-linking agents in epoxy resins:

The compounds mentioned in I were worked-in in an amount of X parts by weight in 100 parts by weight of epoxy based resin Epikote 828 (Shell). The resin was hardened for 2 hours at 80° C. and then for 6 hours at 130° C. Table I describes the results obtained.

TABLE 1

|  | X | Tg(°) | Shore Hardness D (DIN 53505) |
| --- | --- | --- | --- |
| 1,3 DIPMEA | 56.3 | 136 | 84 |
| 1,3 DIPDEA | 60.0 | 72 | 78 |
| 1,3 DIPMIPA | 60.0 | 139 | 86 |
| 1,3 DIPDIPA | 67.4 | 117 | 80 |
| 1,4 DIPDEA | 60.0 | 127 | 82 |

Note: Tg = glass transition temperature

III. Testing of the compounds mentioned in I as chain lengthening agents for polyurethanes:

The representatives of the compounds mentioned in I were tested in the following TDI prepolymers:

Prepolymer A was produced in a way usual to one skilled in the art by reaction of 1 mol of polycaprolactone CAPA 205 (Interox) having with an average molecular weight of 830 and 2 mol of 2,4 toluene diisocyanate (TDI). A prepolymer with a content of free NCO groups of 6.5 percent was obtained.

Prepolymer B was prepared corresponding to prepolymer A; only the polycaprolactone was substituted by 1 mol of polytetrahydrofuran Terathane® 1000 (Du Pont) having an average molecular weight of 1000. A prepolymer with a content of free NCO groups of 6.3 percent was obtained.

The test piece was produced by reaction of 100 parts by weight of prepolymer A or B with X parts by weight of the corresponding compound from I at approximately 60° C. Table 2 represents the results obtained for prepolymer A; Table 3 for prepolymer B.

TABLE 2

|  | X | Shore Hardness D DIN 53505 | Elongation at break [%] DIN 53360 | Tensile strength [N/mm$^2$] DIN 53455 | Resistance to tear propagation [N/mm] DIN 53356 |
|---|---|---|---|---|---|
| 1,3 DIPDEA | 35.5 | 50 | 304 | 33.94 | 81 |
| 1,3 DIPMIPA | 37 | 55 | 299 | 31.3 | 101 |

TABLE 3

|  | X | Shore Hardness D DIN 53505 | Elongation at break [%] DIN 53360 | Tensile strength [N/mm$^2$] DIN 53455 | Resistance to tear propagation [N/mm] DIN 53356 |
|---|---|---|---|---|---|
| 1,3 DIPDEA | 34.5 | 43 | 484 | 49.12 | 68 |
| 1,3 DIPDIPA | 40 | 52 | 319 | 35.22 | 80 |
| 1,3 DIPMIPA | 34 | 60 | 452 | 39.72 | 68 |

What is claimed is:

1. Process for the production of 4,4'-(phenylenediisopropyl)bis(2,6-dialkylanilines) of formula:

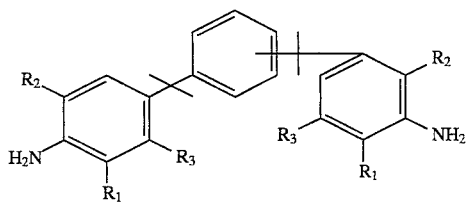

I wherein $R_1$ and $R_2$ are the same or different and each is a ($C_1$–$C_4$)-alkyl group, $R_3$ is a hydrogen or halogen atom, and the central phenylene function is substituted in the 1,3 or 1,4 position, comprising reacting a diisopropenyl benzene of formula:

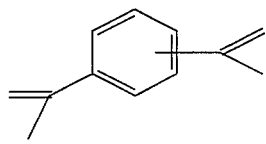

II wherein the isopropenyl groups on the aromatic nucleus are in the 1,4 or 1,3 position to one another, in the presence of aluminum chloride as a catalyst is reacted with an aniline of formula:

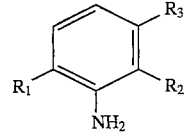

III wherein $R_1$, $R_2$ and $R_3$ have the above-mentioned meanings, the reaction is carried out with exclusion of water at a temperature between 120° and 200° C., the aluminum chloride is used in an amount of 0.02 to 0.3 mol, relative to 1 mol of the aniline of formula III, and the diisopropenyl benzene of formula II, relative to the aniline of formula III, is used in an excess of 10 to 100 percent.

2. The process according to claim 1 wherein the 4,4'-(phenylenediisopropyl)-bis(2,6-dialkylaniline) of formula I is 4,4'-(phenylene-1,3-diisopropyl)-bis(2-isopropyl-6-methylanaline).

3. The process according to claim 1 wherein the reaction is carried out at a temperature between 140° and 160° C.

4. The process according to claim 1 wherein the aluminum chloride is used in an amount of 0.05 to 0.20 mol, relative to 1 mol of the aniline of formula II.

* * * * *